United States Patent [19] [11] 4,187,242
Chalk [45] Feb. 5, 1980

[54] CATALYTIC AROMATIC CARBONATE PROCESS

[75] Inventor: Alan J. Chalk, Kinnelon, N.J.

[73] Assignee: General Electric Company, Schenectady, N.Y.

[21] Appl. No.: 892,497

[22] Filed: Apr. 3, 1978

Related U.S. Application Data

[63] Continuation-in-part of Ser. No. 731,495, Dec. 12, 1976, abandoned.

[51] Int. Cl.$^2$ .............................................. C07C 68/00
[52] U.S. Cl. ................................... 260/463; 528/196; 528/219
[58] Field of Search .................... 260/463, 47 XA; 528/219

[56] References Cited

U.S. PATENT DOCUMENTS

| Re. 29,338 | 9/1976 | Perrotti | 260/463 |
| 3,114,762 | 12/1963 | Mador et al. | 260/463 |
| 4,096,168 | 6/1978 | Hallgren | 260/463 |
| 4,096,169 | 6/1978 | Chalk | 260/463 |

Primary Examiner—Donald G. Daus
Assistant Examiner—M. C. Eakin
Attorney, Agent, or Firm—F. Wesley Turner; Joseph T. Cohen; Leo I. MaLossi

[57] ABSTRACT

Catalytic aromatic carbonate process which comprises contacting a phenol, carbon monoxide, an oxidant, a base, and a Group VIIIB element selected from ruthenium, rhodium, palladium, osmium, iridium or platinum. The resulting aromatic mono- and polycarbonates are useful in the preparation of polycarbonates or as polycarbonates, per se, respectfully, which can be molded or formed into films, sheets, fibers, laminates or reinforced plastics by conventional techniques.

22 Claims, No Drawings

CATALYTIC AROMATIC CARBONATE PROCESS

CROSS REFERENCE TO RELATED APPLICATIONS

This application is a continuation-in-part of Ser. No. 731,495, filed Oct. 12, 1976, abandoned.

This invention is related to my U.S. patent application Ser. No. 731,496 filed Oct. 12, 1976, now U.S. Pat. No. 4,096,169 issued June 20, 1978 and J. E. Hallgren's U.S. patent application Ser. Nos. 834,534 filed Sept. 19, 1977, a continuation of 731,443 filed Oct. 12, 1976, now abandoned; 892,509 filed concurrently herewith, a continuation-in-part of Ser. No. 731,494 filed Oct. 12, 1976, now abandoned; and 731,493 filed Oct. 12, 1976 now U.S. Pat. No. 4,096,168, issued June 20, 1978. All of the aforesaid applications are assigned to the same assignee as the assignee of this application.

BACKGROUND OF THE INVENTION

1. Field of the Invention

This invention relates to a catalytic aromatic carbonate process comprising contacting a phenol, carbon monoxide, an oxidant, a base, and a Group VIIIB element selected from ruthenium, rhodium, palladium, osmium, iridium or platinum to form a reaction mixture. The aromatic carbonate can be isolated or separated from the reaction mixture.

2. Description of the Prior Art

Mador et al. in U.S. Pat. No. 3,114,762, issued Dec. 17, 1963, describes the preparation of aliphatic carbonates by the reaction of aliphatic alcohols with carbon monoxide carried out in the presence of a salt of palladium or platinum metal.

Perrotti et al. in U.S. Pat. No. 3,846,468, issued Nov. 5, 1974, describes the preparation of carbonic acid esters by the reaction of an alcohol with carbon monoxide and oxygen carried out in the presence of copper complexed with an organic molecule. Although the disclosure of Perrotti et al. suggests that elements such as iron cobalt and nickel are effective catalysts in the reaction of alcohols with carbon monoxide in the presence of oxygen, it was found that when iron, cobalt or nickel compounds are substituted for the Group VIIIB elements employed in my process for making aromatic carbonates, such carbonates could not be obtained under these conditions.

DESCRIPTION OF THE INVENTION

This invention embodies a catalytic aromatic carbonate process which comprises contacting a phenol, carbon monoxide, an oxidant, a base, and a Group VIIIB element selected from ruthenium, rhodium, palladium, osmium, iridium or platinum.

The reactants and the resulting reaction products of my process can be illustrated by the following general equations which are furnished for illustrative purposes only since the intermediate (Eq. 1a, 1b, and 1c, or Eq. 2a, 2b, and 2c) reaction mechanisms involved in the preparation of aromatic monocarbonates (Eq. 1) and polycarbonates (Eq. 2) may be much more complex:

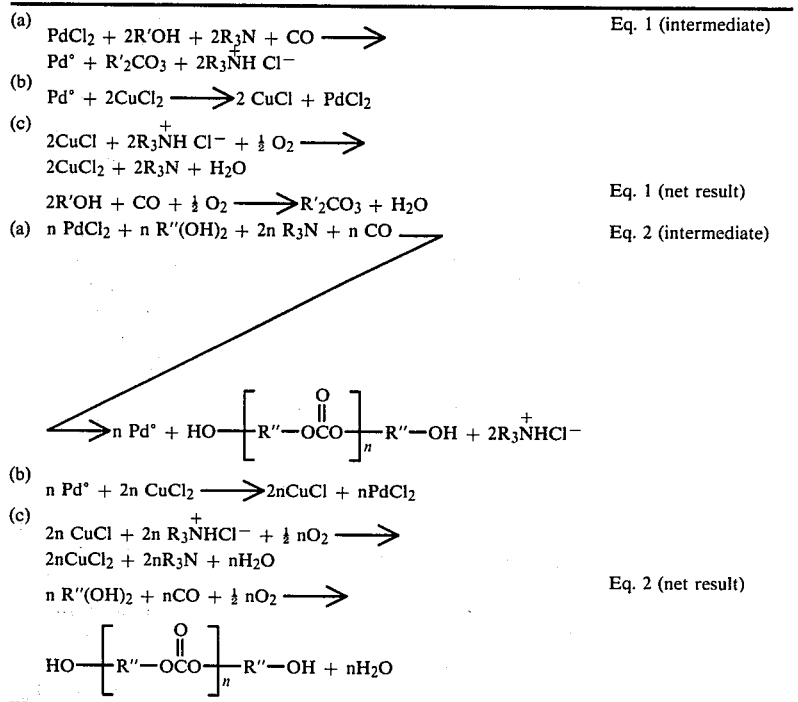

wherein R is an alkyl radical (including cycloalkyl), R' is an aryl radical, R" is an arene radical, and n is a number at least equal to 1.

Any nuclearly hydroxy substituted aromatic compound can be used in my process and is defined herein and in the appended claims as "a phenol". Illustratively the phenol (or phenolic reactants) can be described by the formula:

$$R_a\text{---}(OH)_x,\qquad \text{I.}$$

wherein $R_a$ represents an aromatic radical, where the —OH radical is attached directly to an aromatic ring carbon atom and x is a number being at least equal to 1, advantageously from 1 to 4, and preferably from 1 to 2. The $R_a$ radical can be carbo- or hetero-monocyclic, polycyclic, or fused polycyclic, and can have two or more cyclic systems (monocyclic, polycyclic or fused polycyclic systems) which are connected to each other or by bi- or multivalent radicals.

Preferred phenolic reactants are phenols containing from 6 to 30, and more preferably from 6 to 15 carbon atoms. Illustrative of commercially important phenolic reactants included within the above description are the following: phenol itself (hydroxy benzene), napthol, ortho-, meta-, or paracresol, catechol, cumenol, xylenol, resorcinol, the various isomers of dihydroxydiphenyl, the isomers of dihydroxynaphthalene, bis(4-hydroxyphenyl)propane-2,2,α,α'-bis(4-hydroxyphenyl)p-diisopropylbenzene, 4,4'-dihydroxy-3,5,3',5'-tetrachloro-phenyl-propane-2,2,4,4'-dihydroxy-3,5,3',5'-tetrachloro-phenyl-propane-2,2 and 4,4'-dihydroxy-3,5,3',5'-tetrachloro-phenyl-propane-2,2 and 4,4'-dihydroxy-3,5,3',5'-tetrabromo-phenylpropane-2,2,phloroglucinol, dihydroxy oligomers, for example an oligomer derived from bisphenol-A, etc.

A generally preferred bisphenol that can be used in may process can be described by the following formula:

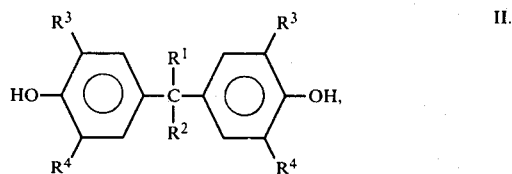

where $R^1$ and $R^2$ are hydrogen, $C_{1-4}$ alkyl or phenyl, at least one of $R^3$ is hydrogen and the other is hydrogen or $C_{1-4}$ alkyl, and at least one of $R^4$ is hydrogen and the other is hydrogen or $C_{1-4}$ alkyl. Especially preferred is bis(2-hydroxyphenyl) propane-2,2, also commonly known as "bisphenol-A" (BPA).

Any Group VIIIB element, defined herein and in the appended claims as "the Group VIIIB element", can be employed subject to the proviso that it is selected from ruthenium, rhodium, palladium, osmium, iridium or platinum. The Group VIIIB elements can be employed in any of their well-known oxidation states as well as their zero valent elemental, i.e. metallic, form.

Illustratively, the Group VIIIB elements can be present in ionic, inorganic or organic compound or complex, etc. forms. The Group VIIIB elements can be employed in oxide, halide, nitrate, sulfate, oxalate, acetate, carbonate, propionate, hydroxide, tartrate, etc., forms.

The Group VIIIB elements can be employed in complex form, e.g. with ligands, such as carbon monoxide, nitriles, tertiary amines, phosphines, arsines, or stibines, etc., and illustratively are often represented by those skilled in the art as mono-, di-, or poly-nuclear Group VIIIB element forms. Generally, the dimeric or polymeric forms are considered to contain Group VIIIB atoms bridged by ligands, halogens, etc. Preferably the Group VIIIB elements form homogeneous mixtures when combined with the phenolic reactants, especially when the process is carried out under liquid phase reaction conditions.

Illustrative of the generally preferred Group VIIIB element, compounds or complexes that can be used in my process follow: Ru, $RuCl_2$, $RuBr_2$, $RuI_2$, $Ru(CO)_2Cl_2$, $Ru(CO)_2I_2$, $Ru(CO)_4Cl_2$, $Ru(CO)_4Br_2$, $Ru(CO)_4I_2$, $RuCl_3$, $RuBr_3$, $RuI_3$, etc., Pd, $PdCl_2$, $PdBr_2$, $PdI_2$, $[Pd(CO)Cl_2]_2$, $[Pd(CO)Br_2]_2$, $[Pd(CO)I_2]_2$, $(C_6H_5CN)_2PdCl_2$, $PdCl_4$, $Pd(OH)_2(CNC_4H_9)_2$, $PdI_2(CNC_6H_5)_2$, $Pd(OH)_2(CNCH_3OC_6H_5)_2$, $Pd(CNC_4H_9)_4$, etc., Rh, $Rh(CO)Cl_2$, $Rh(CO)Br_2$, $Rh(CO)I_2$, $Rh_2Cl_2(CO)_2$, $Rh_2(CO)_4Cl_2$, $Rh_2(CO)_4Br_2$, $Rh_2(CO)_4I_2$, $[Rh(CO)_2Cl]_2$, $RhCl_3$, $RhBr_3$, $RhI_3$, etc., Os, $Os(CO)_3Cl_2$, $Os(CO)_3Br_2$, $Os(CO)_3I_2$, $Os(CO)_4Cl_2$, $Os(CO)_4Br_2$, $Os(CO)_4I_2$, $Os(CO)_8Cl_2$, $Os(CO)_8Br_2$, $Os(CO)_8I_2$, $OsCl_2$, $OsCl_3$, $OsI_2$, $OsI_3$, $OsBr_3$, $OsBr_4$ and $OsCl_4$, etc., Ir, $IrCl_3$, $IrCl_3(CO)$, $Ir_2(Co)_8$, $IrCl_3$, $IrBr_3$, $IrCl_3$, $IrBr_4$, $IrI_4$, etc., Pt, $PtCl_2$, $PtBr_2$, $PtI_2$, $Pt(CO)_2Cl_2$, $Pt(CO)_2Br_2$, $Pt(CO)_2I_2$, $Pt(CO)_2Cl_4$, $Pt(CO)_2Br_4$, $Pt(CO)_2I_4$, $Pt(CO)_3Cl_4$, $Pt(CO)_3Br_4$, $Pt(CO)_3I_4$, $PtCl_2(CNC_6H_5)_2$, etc.

Illustrative of ligands that can be associated with the Group VIIIB elements in complex form—other than and, optionally, in addition to carbon monoxide—include organic tertiary amines, phosphines, arsines and stibine ligands of the following formula:

$$(E)_3Q,$$

wherein, independently, each E is selected from the radicals Z and OZ, where independently each Z is selected from organic radicals containing from 1 to 20 carbon atoms, and wherein independently each Q is selected from nitrogen, phosphorus, arsenic or antimony. Preferably, the organic radicals are free of active hydrogen atoms, reactive unsaturation, and are oxidatively stable. More preferably, the E groups are alkyl, cycloalkyl and aryl radicals and mixtures thereof, such as alkaryl, aralkyl, alkcycloalkyl containing from 1 to 10 carbon atoms, and even more preferably each E is an aryl group containing from 6 to 10 carbon atoms.

Illustrative of the generally known presently preferred Group VIIIB complexes which contain ligands include the following: $RuCl_2[P(C_6H_5)_3]_4$, $[Rh(CO)_2Cl]_2$, $trans[(C_2H)_5P]_2PdBr_2$, $[P(C_4H_9)_3]_2PdCl_4$, $[(C_6H_5)_3P]_3IrCl_3(CO)$, $[(C_6H_5)_3As]_3IrCl_3(CO)$, $[(C_6H_5)_3Sb]_3IrCl_3(CO)$, $[(C_6H_5)_3P]_2PtCl_2$, $[(C_6H_5)_3P]_2PtF_2$, $[(C_6H_5)_3P]_2PtF_2(CO)_2$, $Pt[(C_6H_5)_3P]_2(CO)_2$, etc.

The Group VIIIB element compounds and/or complexes can be prepared by any method well-known to those skilled in the art including the methods referenced in the following publications:

*Treatise on Inorganic Chemistry*, Volume II, H. Remy, Elsevier Publishing Co. (1956);

*Reactions of Transition-Metal Complexes*, J. P. Candlin, K. A. Taylor and D. T. Thompson, Elsevier Publishing Co. (1968) Library of Congress Catalog Card No. 67-19855;

*Organic Syntheses Via Metal Carbonyls*, Vol. 1, I. Wender and P. Pino, Interscience Publishers (1968) Library of Congress Catalog Card No. 67-13965;

*The Organic Chemistry of Palladium*, Vols. I and II, P. M. Maitlis, Academic Press (1971) Library of Congress Catalog Card No. 77-162937;

*The Chemistry of Platinum and Palladium*, F. R. Hartley, Halsted Press (1973);

The process can be carried out in the absence of any solvent, e.g. where the phenolic reactant acts as both a reactant and a solvent, however preferably is carried out in the presence of a solvent, and more preferably solvents of the general class: methylene chloride, ethylene dichloride, chloroform, carbon tetrachloride, tetrachloroethylene, nitromethane, hexane, 3-methylpentane, heptane, cyclohexane, methylcyclohexane, cyclohexane, isooctane, p-cymene, cumene, decalin, toluene, benzene, diphenylether, dioxane, thiophene, dimethyl sulfide, ethyl acetate, tetrahydrofuran, chlorobenzene, anisol, bromobenzene, o-dichlorobenzene, methyl formate, iodobenzene, acetone, acetophenone, etc., and mixtures thereof.

In general, the process can be carried out in any basic reaction medium, preferably, that provided by the presence of any inorganic or organic base or mixtures thereof. Representative of basic species which can be employed are the following: elemental alkali and alkaline earth metals; basic quaternary ammonium, quaternary phosphonium or tertiary sulfonium compounds; alkali or alkaline earth metal hydroxides; salts of strong bases and weak acids; primary, secondary or tertiary amines; etc. Specific examples of the aforementioned are sodium, potassium, magnesium metals, etc.; quaternary ammonium hydroxide, tetraethyl phosphonium hydroxide, etc.; sodium, potassium, lithium, and calcium hydroxide; quaternary phosphonium, tertiary sulfonium, sodium, lithium, and barium carbonate, sodium acetate, sodium benzoate, sodium methylate, sodium thiosulfate, sodium sulfide, sodium tetrasulfide, sodium cyanide, sodium hydride, sodium borohydride, potassium fluoride, triethylamine, trimethylamine, allyldiethylamine, benzyldimethylamine, dioctylbenzylamine, dimethylphenethylamine, 1-dimethylamino-2-phenylpropane, N,N,N',N'-tetramethylenediamine, 2,2,6,6-tetramethylpyridine, N-methyl piperidine, pyridine, 2,2,6,6,N-pentamethylpiperidine, etc. Especially preferred bases are sterically hindered amines, e.g. diisopropylmonoethylamine, 2,2,6,6,N-pentamethylpiperidine, etc.

Any oxidant can be employed in the herein claimed process subject to the proviso that the oxidant has an oxidation potential greater than or more positive then "the Group VIIIB element". Preferred oxidants comprise any element, compound or complex of a periodic Group IIIA, IVA, VA, VIA, VIIA, IB, IIB, IVB, VB, VIB, VIIB, VIIIB, lanthanides or actinide having an oxidation potential greater than or more positive than "the Group VIIIB element". Typical well-known oxidants of "the Group VIIIB elements" are compounds or complexes of copper, iron, manganese, cobalt, mercury, lead, cerium, vanadium, uranium, bismuth, chromium, etc. Of these, copper oxidants are preferred. Wherein the oxidant is employed in salt form, the anion portion of the salt may be a $C_{1-20}$ carboxylate, halide, nitrate, sulfate, etc., and preferably is a halide, e.g., chloride, bromide, iodide, or fluoride. Illustrative of typical oxidants are cupric chloride, cupric bromide, cupric nitrate, cupric sulfate, cupric acetate, etc. In addition to the compounds described above, elements commonly employed as oxidants in elemental form, e.g. oxygen, ozone, chlorine, bromine, fluorine, etc., may be employed as the sole oxidant in the herein claimed process. Frequently, compounds or complexes of a periodic Group IIIA, IVA, VA, VIA, VIIA, IB, IIB, IVB, VB, VIB, VIIB, VIIIB, lanthanide or actinide are preferably employed as a redox co-catalyst of a periodic Group VIA or VIIA element, e.g. oxygen, sulfur, selenium, fluorine, chlorine, bromine, iodine, etc., including mixtures thereof, in order to enhance the rate of oxidation of "the Group VIIIB element".

As used herein and in the appended claims, the expression "complexes" includes coordination or complex compounds well-known to those skilled in the art such as those described in *Mechanisms of Inorganic Reactions*, Fred Basolo and Ralph G. Pearson, 2nd Edition, John Wiley and Sons, Inc. (1968). These compounds are generally defined herein as containing a central ion or atom, i.e. a periodic Group IIIA, IVA, VA, VIA, VIIA, IB, IIB, IVB, VB, VIB, VIIB, VIIIB, lanthanide or actinide element and a cluster of atoms or molecules surrounding a periodic group element. The complexes may be nonionic, or a cation or anion, depending on the charges carried by the central atom and the coordinated groups. The coordinated groups are defined herein as ligands, and the total number of attachments to the central atom is defined herein as the coordination number. Other common names for these complexes include complex ions (if electrically charged), Werner complexes, coordination complexes or, simply, complexes.

The redox co-catalysts as a class comprise any element, compound or complex which catalyze the oxidation of "the Group VIIIB element", i.e. ruthenium, rhodium, palladium, osmium, iridium or platinum, in the presence of any oxidant from a lower oxidation state to a higher oxidation state. Preferred redox co-catalysts comprise elements, compounds or complexes of a periodic Group IIIA, IVA, VA, VIA, VIIA, IB, IIB, VB, VIB, VIIB, VIIIB, lanthanide or actinide.

In a presently preferred embodiment oxygen is employed as a sole oxidant in combination with a redox co-catalyst selected from a periodic Group element, compound or complex.

Any source of oxygen can be employed, i.e., air, gaseous oxygen, liquid oxygen, etc. Preferably either air or gaseous oxygen is employed. Also preferably the process is carried out under positive oxygen pressure, i.e., where oxygen is present in stoichiometric amounts sufficient to form the desired aromatic mono- or polycarbonate. In general, oxygen pressures within the range of from about 0.1 to 500 atmospheres, or even higher, can be employed with good results. Presently preferred are oxygen pressures within the range of from about ½ to 200 atmospheres.

Any amount of the oxidant can be employed. For example, oxidant to phenol mole proportions within the range of from about 0.001:1 or lower to about 1000:1 or higher are effective; however, preferably ratios from 0.1:1 to 10:1 are employed to insure an optimum conversion of phenol to aromatic carbonate.

Any amount of redox co-catalyst component can be employed. For example, redox catalyst to phenol mole proportions within the range of from about 0.0001:1 or lower to about 1000:1 or higher are effective; however, preferably ratios of from 0.0001:1 to 1:1, and more preferably 0.001:1 to 0.01:1 are employed.

Any amount of base can be employed. In general, effective mole ratios of base to "the Group VIIIB element" are within the range of from about 0.00001:1 to about 100:1 or higher, preferably from 0.5:1 to about 10:1, and more preferably from 1:1 to 2:1. Generally, mole ratios of at least 1:1 enhance both the reaction rate and the yield of aromatic carbonate.

Any amount of "the Group VIIIB element" can be employed. For example, "the Group VIIIB element" to phenol mole proportions within the range of from about 0.0001:1 or lower to about 1000:1 or higher are effective; however, preferably ratios of from 0.001 to 0.01 are employed in my catalytic reaction.

Any amount of carbon monoxide can be employed. Preferably the process is carried out under positive carbon monoxide pressure; i.e., where carbon monoxide is present in stoichiometric amounts sufficient to form the desired aromatic mono- or polycarbonate. In general, carbon monoxide pressures within the range of from about ½ to 500 atmospheres, or even higher, can be employed with good results. Presently preferred are CO pressures within the range of from 1 to 200 atmospheres.

Any amount of solvent, preferably inert, can be employed. In general, optimum solvent to phenolic reactant mole proportions are from 0.5:99.5 to 99.5:0.5, preferably from 50:50 to 99:1.

Any reaction temperature can be employed. In general, optimum reaction temperatures are 0° C., or even lower, to 200° C., or even higher and more often 0° C. to 50° C.

Any reaction time period can be employed. Generally optimum reaction time periods are about 0.1 hour or even less to about 10 hours or even more.

Following some of the procedures described herein, aromatic salicylates can be formed. These aromatic salicylates, i.e. aromatic compounds which can be defined as "salicylate", can be generically described by the following formula:

$$HO-R_b-\overset{\overset{O}{\|}}{C}-O-R_c,$$

wherein $R_b$ represents an aromatic radical wherein the hydroxyl radical is positioned ortho relative to the carboxylate, i.e.

$$-\overset{\overset{O}{\|}}{C}-O-$$

radical, and $R_c$ represents an aromatic radical. The $R_b$ and $R_c$ radicals can be carbo- or hetero-monocyclic, polycyclic, or fused polycyclic, and can have two or more cyclic systems (monocyclic, polycyclic or fused polycyclic systems) which are directly joined to each other by single or double valence bonds, or by bi- or multivalent radicals.

The separation and recovery of the salicylates is described in the U.S. patent application Ser. No. 731,443 of J. E. Hallgren, filed Oct. 12, 1976.

In order that those skilled in the art may better understand my invention, the following examples are given which are illustrative of the best mode of this invention, however, these examples are not intended to limit the invention in any manner whatsoever. In the examples, unless otherwise specified, all parts are by weight and the reaction products were verified by infrared spectrum, C-13 nuclear magnetic resonance and mass spectrometry.

EXAMPLE I

Preparation of 4,4'-(α,α-dimethylbenzyl)diphenyl carbonate using p-cumylphenol, carbon monoxide, diisopropylmonoethylamine, metallic palladium, and copper dibromide.

A reaction pressure vessel was charged with 2.211 g. (10.43 mmol.) of p-cumylphenol, 0.126 g. (1.18 mmol.) of palladium metal, i.e. palladium having an oxidation state of zero, 1.330 g. (10.31 mmol.) of diisopropylmonoethylamine, 1.110 g. (5.0 mmol.) of copper dibromide, 20 ml. of methylenedichloride, and sufficient carbon monoxide to charge the vessel to 66 psi. Subsequent workup showed the presence of 0.141 g. (6% yield) of 4,4'-(α,α-dimethylbenzyl)dimethylbenzyl)-diphenylcarbonate of the formula

EXAMPLE II

The preparation of 4,4'-(α,α-dimethylbenzyl)diphenyl carbonate using bis(benzonitrile)palladium(II)dichloride.

The reaction medium contained 2.28 g. (10.46 mmol.) of p-cumylphenol, 0.3 g. (0.22 mmol.) of bisbenzonitrilepalladium(II)dichloride, 1.342 g. (10.42 mmol.) of diisopropylmonoethylamine, 1.288 g. (5.78 mmol.) of copper dibromide, 20 ml. of methylene chloride, and sufficient carbon monoxide to charge the vessel to 70 psi. The subject product yield was 11% of 4,4'-(α,α-dimethylbenzyl)diphenylcarbonate.

The number of carbonate moieties, i.e.

$$-O-\overset{\overset{O}{\|}}{C}-O-$$

formed per mole of palladium metal was 5.2, which hereafter is referred to as the Group VIIIB "turnover value" of the reaction.

EXAMPLE III

Preparation of 4,4'-(α,α-dimethylbenzyl)diphenylcarbonate under carbon monoxide and oxygen pressure.

The reaction medium contained p-cumylphenol, bis(benzonitrile)palladium(II) dichloride, diisopropylmonoethylamine, and copper dibromide in the following mole proportions: 100:2:15:8. Sufficient carbon monoxide was charged to the vessel to raise the pressure to 31 psi and sufficient oxygen was subsequently added to raise the pressure of the vessel to a total pressure of 62 psi. The product yield was 8% of 4,4'-α,α(-dimethylbenzyl)diphenylcarbonate. The turn over value was 4.

EXAMPLE IV

Preparation of 4,4'-(α,α-dimethylbenzyl)diphenylcarbonate using palladium(I) monocarbonylmonobromide and 2,2,6,6,N-pentamethylpiperidine as a base.

The reaction vessel contained 2.12 g. (10.0 mmol.) of p-cumylphenol, 1.55 g. (10.0 mmol.) of the 2,2,6,6,N-pentamethylpiperidine, 2.233 g. (10.0 mmol.) copper dibromide, 0.1 g. (0.5 mmol.) of palladium(I) monocarbonylmonobromide, and 20 ml. of methylenechloride. The product yield was 0.60 g. (26%) of aromatic carbonate and 0.54 g. (18%) of mono-bromo-p-cumylphenol. The turnover value was 5.4.

EXAMPLE V

This procedure, not an example of this invention, illustrates the attempted preparation of diphenylcarbonate employing the teachings of Perrotti et al. Re. 29,338 issued Aug. 2, 1977 formerly, U.S. Pat. No. 3,346,468, issued Nov. 5, 1974 by contacting sodium phenoxide with carbon monoxide in the presence of pyrridine as a base.

The procedure involved the addition of 6.73 g. (0.05 moles) of copper dichloride, 50 ml. of pyridine, and 150 ml. of N,N-dimethylformamide to the reaction medium. The resulting mixture was cooled to −78° C. in a dry ice acetone bath. 11.6 g. (0.10 moles) of sodium phenoxide dissolved in 50 ml. of N,N-dimethylformamide was slowly added to the reaction medium while maintaining the temperature below −50° C. After all of the sodium phenoxide has been added, the mixture was analyzed for evidence of the formation of diphenylcarbonate at the following temperatures. Less than −50° C., −30° C., −10° C., room temperature, +70° C. while carbon monoxide was slowly bubbled through the reaction medium. Gas chromatagraphy of the reaction medium during the entire reaction period showed no aromatic carbonate formation and showed only the starting materials present within the reaction medium. From this experimental data, it was concluded that teachings of the Perrotti et al. reference were not applicable to reactions involving phenolic reactants.

In a preferred embodiment of my invention, set out in Examples V to XV, my process is carried out in the presence of oxygen and a molecular sieve. This embodiment, which is the subject matter of J. E. Hallgren's U.S. patent application Ser. No. 731,494, filed Oct. 12, 1976, now abandoned, has been found to provide improved results and so is disclosed also herein, although not essential to the utility of this invention. Particularly useful molecular sieves are those designated by the Linde Division of the Union Carbide Corporation as zeolite types A, X and Y, described in U.S. Pat. Nos. 2,882,243, 3,130,007 and 3,529,033, which descriptions are also incorporated herein in their entirety by reference.

EXAMPLE VI

Preparation of 4,4′($\alpha,\alpha$-dimethylbenzyl)diphenylcarbonate under carbon monoxide and oxygen pressure and in the presence of a molecular sieve Type 4A—a commercial product of Union Carbide Corporation of the general chemical formula 0.96±0.04 $Na_2O$.1.00 $Al_2O_3$.1.92±0.09 $SiO_2$.x $H_2O$.

The reaction medium contained p-cumylphenol, bis(benzonitrile)palladium(II) dichloride, diisopropylmonoethylamine, and copper dibromide in the following mole proportions: 100:2:16:8. Sufficient carbon monoxide was charged to the vessel to raise the pressure to 31 psi and sufficient oxygen was subsequently added to raise the pressure of the vessel to a total pressure of 62 psi. The product yield was 31% of 4,4′-$\alpha,\alpha$(-dimethylbenzyl)diphenylcarbonate. As illustrated by this example, inclusion of a molecular sieve significantly increases the yield of aromatic carbonate as illustrated by the 400% improvement in yield by this example contrasted with the yield of Example III.

In a preferred embodiment of my invention set out in Examples VII, VIII and XII my process is carried out through the use of a manganese or cobalt complex catalyst. The embodiment, which is the subject matter of J. E. Hallgren's U.S. patent application Ser. No. 731,494, filed Oct. 12, 1976, now abandoned, has been found to provide improved results and so is disclosed also herein, although not essential to the utility of this invention.

Illustrative of manganese complexes are those commonly referred to as manganese chelates and includes those represented by the general formula LMn, wherein L is a ligand derived from an ω-hydroxyoxime or an orthohydroxyareneoxime, including mixtures thereof, and Mn is the transition metal manganese. Illustratively, the manganese can be employed in any of its oxidation states, e.g. from −1 to +7.

An ω-hydroxyoxime ligand, represented as "L" in the general formula LMn, can be described by the following formula:

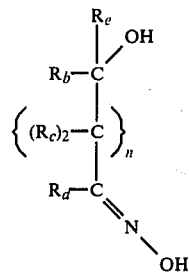

wherein independently each $R_b$, $R_c$, $R_d$ and $R_3$ is selected from the group consisting of hydrogen, acyclic and cyclic hydrocarbon radicals, and n is a positive integer equal to 0 or 1.

An ortho-hydroxyareneoxime ligand, represented as "L" in the general formula LMn, can be described by the following formula:

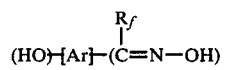

wherein $R_f$ is independently selected from the group consisting of hydrogen and acyclic hydrocarbon radicals, Ar is at least a divalent arene radical having at least one —OH radical and at least one

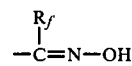

radical attached directly to an ortho position arene ring carbon atom. Methods for the preparation of manganese chelate complexes including mixtures thereof are described in U.S. Pat. Nos. 3,956,242, 3,965,069 and 3,972,851, etc. The description of the manganese complexes as set out therein are incorporated herein in their entirety by reference.

Illustrative of generally preferred manganese chelate complexes are described by the following formulas:

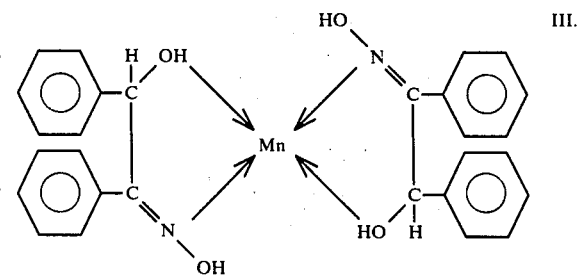

-continued

IV.
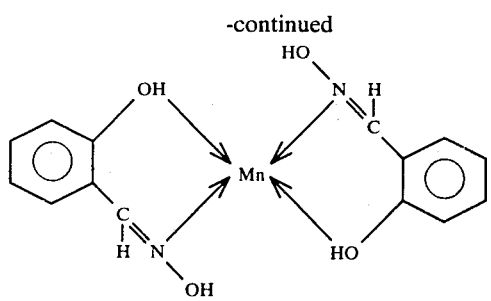

Illustrative of cobalt complexes which are preferred oxidants are those commonly referred to as cobalt chelates and includes those represented by the general formula:

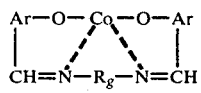

wherein Ar represents a divalent arene radical and $R_g$ represents a divalent organic radical containing at least 2 carbon atoms. Methods for the preparation of cobalt chelate complexes including mixtures thereof are described in U.S. Pat. Nos. 3,455,880, 3,444,133 and 3,781,382, etc. The description of the cobalt complexes as set out therein are incorporated herein in their entirety by reference.

Generally presently preferred cobalt chelate complexes are described by the following formulas:

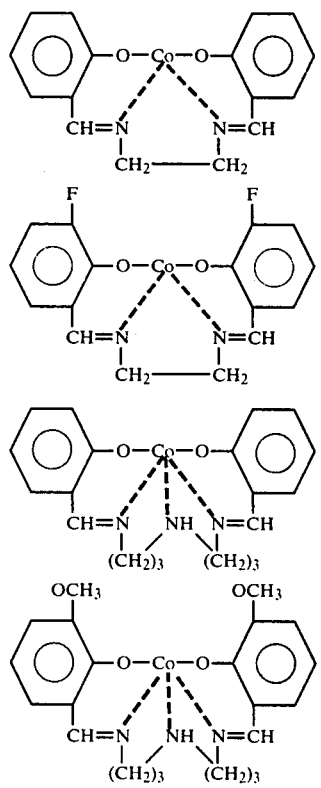

VI.

VII.

VIII.

IX.

-continued

X.
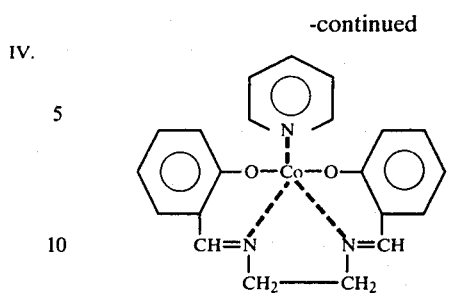

EXAMPLE VII

Preparation of 4,4'-(α,α-dimethylbenzyl)diphenylcarbonate using p-cumylphenol, carbon monoxide, the 2,2,6,6,N-pentamethylpiperidine and a palladium bromide complex with bis(benzoinoxime) manganese(II) and a molecular sieve.

A reaction vessel was charged with 2.12 g. (0.010 mole) of p-cumylphenol, 0.030 g. (0.00010 moles) of palladiumbromide, 0.051 g. (0.00010 mole) of bis(benzoinoxime)manganese(II), 0.155 g. (0.0010 mole) of the 2,2,6,6,N-pentamethylpiperidine compound, 30 ml. of methyl chloride and 2.0 g. of a Lindy Union Carbide 3A molecular sieve which had been activated at 200° C. in vacuo. The type 3A molecular sieve employed is a commercial product of Union Carbide Corporation produced from Type 4A molecular sieves through ionic exchange of about 75% of the sodium ions by potassium. Carbon monoxide and air were bubbled slowly through the reaction vessel mixture at room temperature for 18 hours. Gas chromatography indicated the presence of 0.495 g. (22.2% conversion) of the 4,4'-(α,α-dimethylbenzyl)diphenylcarbonate. After 44 hours, reaction product contained 1.23 g. (55% conversion) of the aromatic carbonate.

EXAMPLES VIII–XV

Following the General Procedure of Example VII, set out hereinbefore, a series of reactions were run employing various oxidants for the preparation of aromatic carbonates in the presence of molecular sieves. Summarized in Table I hereafter are the reaction parameters and products, i.e. the mole proportions of Group VIIIB element: oxidant: phenolic reactant: base, the percent conversion of the phenolic reactant to aromatic carbonate, the reaction time and the turnover value.

In all of the examples, the phenolic reactant was p-cumylphenol and the base was 2,2,6,6,N-pentamethylpiperidine. The Group VIIIB element in Examples VII, VIII, IX and XIII was palladium (II) dibromide, and in Examples X, XI and XII was palladium (I) monocarbonyl monobromide. The oxidant employed in each example is tabulated in Table I. Example XIV was a control run analogous to Example VII except that the Group VIII element was excluded from the reaction and the reaction time was extended. It is consequently not an example of the invention.

TABLE I

| Example No. | Redox Component | Mole Ratios Group VIIIB: | Redox Component: | Phenolic Reactant: | Base | Percent (%) Conversion | Reaction Time (hr) | Turn Over Value |
|---|---|---|---|---|---|---|---|---|
| VII | Mn(II)(benzoinoxime)$_2$ | 1 | 3 | 100 | 20 | 96 | 44 | 54 |
| VIII | Mn(II)(benzoinoxime)$_2$ | 1 | 1 | 100 | 10 | 55 | 44 | 95 |
| IX | (C$_4$H$_9$N)$_2$Mn(II)Br$_4$ | 1 | 3.5 | 100 | 35 | 20 | overnight | 19 |
| X | Mn(II)Br$_2 \cdot$ 4H$_2$O | 1 | 10 | 100 | 100 | 20 | 165 | 19 |
| XI | Cu(I)Br | 1 | 10 | 100 | 20 | 21 | 110 | 20 |
| XII | Co(salen)pyridine | 1 | 3 | 100 | 15 | 90 | 192 | 89 |
| XIII | VBr$_3$ | 1 | 3 | 100 | 15 | 1.7 | 72 | 0.7 |
| XIV | Mn(II)(benzoinoxime)$_2$ | 0 | 3 | 100 | 20 | non-detectable | 168 | 0 |

EXAMPLE XV

Preparation of a polycarbonate of bisphenol-A by contacting bis(4-hydroxyphenyl)propane-2,2, carbon monoxide, manganese(II)bis(benzoinoxime), 2,2,6,6,N-pentamethylpiperidine, palladium(II)dibromide, oxygen, molecular sieve Type 3A and air.

A 50 ml. three-neck flask was charged with 4.56 g. (20.0 mmol.) of bisphenol-A, 0.62 g. (4.4 mmol.) of 2,2,6,6,N-pentamethylpiperidine, 0.06 g. (0.20 mmol.) of palladium(II)dibromide, 0.30 g. (0.60 mmol.) to manganese(II)bis(benzoinoxime), 4 g. of molecular sieve Type 3A and 30 ml. of methylene chloride. Carbon monoxide and air were passed through the solution for 42 hours. Reverse phase liquid chromatography showed the presence of bisphenol-A and bisphenol-A dimers, trimers, pentamers and higher oligomers. An additional 0.06 g. (0.07 mmol.) of palladium(II)dibromide was added and the reaction continued. The $\overline{\text{Mn}}$ number average molecular weight of the polycarbonate was estimated at 2,800 with about a 10% reco ery. This example illustrates and demonstrates the utility of my catalytic process in the preparation of polycarbonates of bisphenol-A.

Although the above examples have illustrated various modifications and changes that can be made in the carrying out of my process, it will be apparent to those skilled in the art that other Group VIIIB metals, phenolic compounds, ligands, oxidants, redox components and solvents as well as other reaction conditions can be effected without departing from the scope of the invention.

I claim:

1. An aromatic carbonate process which comprises contacting a phenol, carbon monoxide, a base, the Group VIIIB element selected from ruthenium, rhodium, palladium, osmium, iridium or platinum, and an oxidant having an oxidation potential greater than that of the said selected Group VIIIB element.

2. The claim 1 process, wherein said Group VIIIB element is present in an ionic form.

3. The claim 1 process, wherein said base is a tertiary amine.

4. The claim 1 process, wherein said Group VIIIB element is associated with a carbonyl group.

5. The claim 1 process, wherein said group VIIIB element is associated with a halide.

6. The claim 1 process, wherein said Group VIIIB element is coordinated with a ligand selected from an arsine, a stibine, a phosphine, a nitrile or a halide.

7. The claim 1 process, wherein said Group VIIIB element is associated with an inorganic halide compound.

8. The claim 1 process, further comprising separating at least a portion of resulting aromatic carbonate product.

9. The claim 1 process in which the phenol is p-cumylphenol, the base is 2,2,6,6,N-pentamethylpiperidine, the oxidant is oxygen, the Group VIIIB element is palladium in the form of palladium dibromide, and further comprising a redox co-catalyst for the oxidation of said Group VIIIB element.

10. The process of claim 1 in which the Group VIIIB element is palladium.

11. The claim 1 process, further comprising, after the preparation of the aromatic carbonate, separating at least a portion of any resulting Group VIIIB element, compound or complex from said carbonate, oxidizing at least a portion of said resulting Group VIIIB element, compound or complex and recycling at least a portion of said oxidized element, compound or complex in said aromatic carbonate process.

12. An aromatic polycarbonate process which comprises contacting an aromatic polyphenol with carbon monoxide, a base, the Group VIIIB element selected from the class consisting of ruthenium, rhodium, palladium, osmium, iridium and platinum, and an oxidant having an oxidation potential greater than that of the said selected Group VIIIB element.

13. An aromatic polycarbonate process which comprises contacting an aromatic bisphenol of the formula:

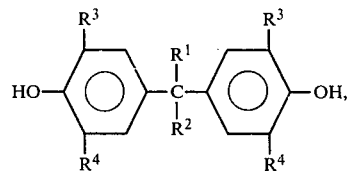

where independently each R$^1$ and R$^2$ is hydrogen, C$_{1-4}$ alkyl or phenyl and independently each R$^3$ and R$^4$ is hydrogen or C$_{1-4}$ alkyl, with carbon monoxide, the Group VIIIB element selected from the class consisting of ruthenium, rhodium, palladium osmium, iridium and platinum and an oxidant having an oxidation potential greater than that of the said selected Group VIIIB element.

14. The claim 13 process, wherein R$^1$ and R$^2$ are methyl and at least one of R$^3$ and R$^4$ is hydrogen.

15. The claim 14 process, wherein the base is a tertiary amine.

16. The claim 15 process, carried out in the presence of an inert solvent.

17. An aromatic polycarbonate process which comprises contacting an aromatic bisphenol of the formula:

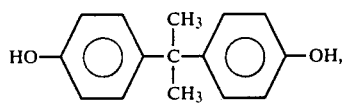

with carbon monoxide, a base, the Group VIIIB metal selected from the class consisting of ruthenium, rhodium, palladium, osmium, iridium and platinum, and an oxidant having an oxidation potential greater than that of the said selected Group VIIIB element.

18. An aromatic monocarbonate process which comprises contacting an aromatic phenol of the formula:

wherein $R_a$ represents an aromatic radical wherein the —OH radical is attached directly to an aromatic ring carbon atom and x is the number 1, with carbon monoxide, a base, the Group VIIIB element selected from the class consisting of ruthenium, rhodium, palladium, osmium, iridium and platinum, and an oxidant having an oxidation potential greater than that of the said selected Group VIIIB element.

19. The claim 18 process, wherein $R_a$ is selected from carbo- or heteromonocyclic, polycyclic or fused polycyclic radicals.

20. The claim 19 process, wherein the base is a tertiary amine.

21. The claim 20 process, carried out in the presence of an inert solvent.

22. An aromatic monocarbonate process which comprises contacting phenol with carbon monoxide, a base, a Group VIIIB element selected from the class consisting of ruthenium, rhodium, palladium, osmium, iridium and platinum, and an oxidant having an oxidation potential greater than that of the said selected Group VIIIB element.

* * * * *